(12) United States Patent
Tsao et al.

(10) Patent No.: US 10,047,466 B2
(45) Date of Patent: Aug. 14, 2018

(54) BANDAGE AND METHOD OF PRODUCING THE SAME

(71) Applicant: Coreleader Biotech Co, Ltd., New Taipei (TW)

(72) Inventors: Teeming Tsao, New Taipei (TW);
Juin-Hong Cherng, Taipei (TW);
Cheng-Che Liu, Taipei (TW);
Shou-Hung Tang, Taipei (TW)

( * ) Notice: Subject to any disclaimer, the term of this patent is extended or adjusted under 35 U.S.C. 154(b) by 667 days.

(21) Appl. No.: 14/084,710

(22) Filed: Nov. 20, 2013

(65) Prior Publication Data

US 2015/0141896 A1    May 21, 2015

(51) Int. Cl.
*A61F 13/00* (2006.01)
*D06B 1/00* (2006.01)
*A61L 15/22* (2006.01)
*D06M 13/188* (2006.01)
*D06M 13/192* (2006.01)
*D06M 13/207* (2006.01)

(52) U.S. Cl.
CPC .......... *D06B 1/00* (2013.01); *A61F 13/00991* (2013.01); *A61L 15/225* (2013.01); *D06M 13/188* (2013.01); *D06M 13/192* (2013.01); *D06M 13/207* (2013.01)

(58) Field of Classification Search
CPC .................................. A61F 13/00; D06B 1/00
See application file for complete search history.

(56) References Cited

U.S. PATENT DOCUMENTS

| | | | | |
|---|---|---|---|---|
| 6,471,982 B1* | 10/2002 | Lydon | ................... | A61L 15/225 424/443 |
| 8,899,277 B2* | 12/2014 | Chiu | ...................... | D02G 3/449 139/383 R |
| 2005/0240137 A1* | 10/2005 | Zhu | ..................... | A61B 17/0057 602/56 |

* cited by examiner

*Primary Examiner* — Andrew Piziali

(57) ABSTRACT

A method for fabricating a bandage comprises the following steps: preparing multiple complex yarns each comprising chitosan fibers and rayon fibers; (b) weaving solely the multiple complex yarns to form a preformed bandage; (c) immersing the preformed bandage in an acid alcohol, and then washing the preformed bandage by alcohol to obtain an alcohol-washed bandage; and, (d) heating the alcohol-washed bandage to obtain the bandage. The bandage related to the method is comprised of complex yarns, wherein each of the complex yarns is composed of chitosan fibers and rayon fibers. By means of immersing the preformed bandage into an acid alcohol, the bandage thus obtained has enhanced tensile strength, decreased dissolution rate and reduced hemolytic dose.

9 Claims, 1 Drawing Sheet

```
PREPARING MULTIPLE COMPLEX YARNS EACH
INCLUDING CHITOSAN FIBERS AND RAYON
FIBERS
            │
            ▼
WEAVING SOLELY THE MULTIPLE COMPLEX
YARNS TO FORM A PREFORMED BANDAGE
            │
            ▼
IMMERSING THE PREFORMED BANDAGE IN AN
ACID ALCOHOL, AND THEN WASHING THE
BANDAGE BY ALCOHOL TO OBTAIN AN
ALCOHOL-WASHED BANDAGE
            │
            ▼
HEATING THE ALCOHOL-WASHED BANDAGE
TO OBTAIN THE BANDAGE
```

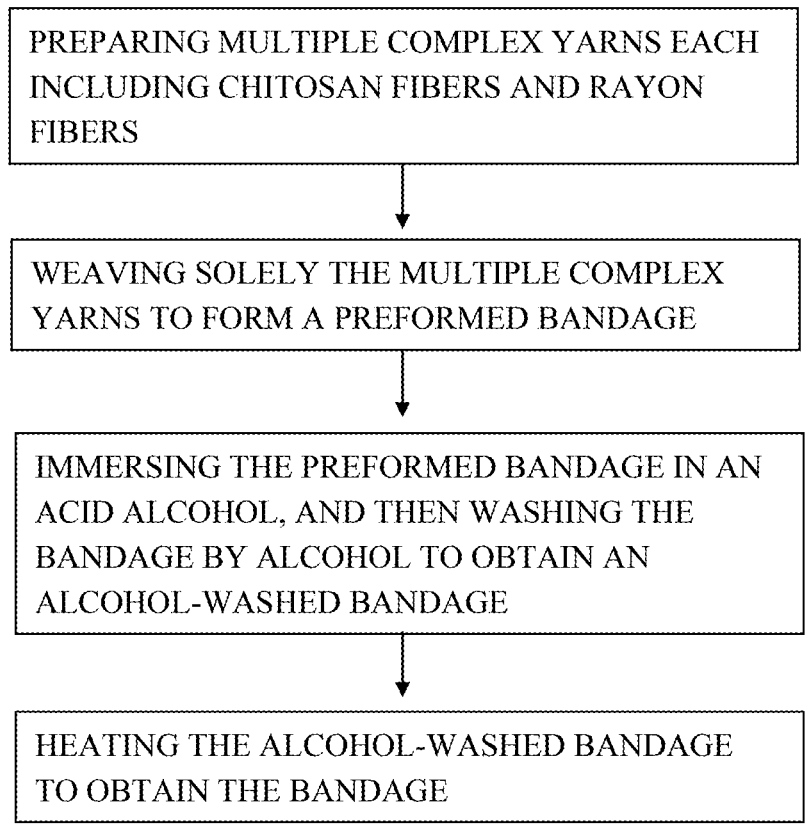

BANDAGE AND METHOD OF PRODUCING THE SAME

BACKGROUND OF THE INVENTION

1. Field of the Invention

The present invention relates to a wound dressing, and more particularly to a bandage.

2. Description of the Prior Arts

The conventional method for fabricating a bandage containing chitosan is coating a solution or powder of chitosan to a non-woven fabric made from cotton fibers or synthetic fibers. The fabricating method is easy and simple, but the chitosan would easily remain on a surface of the non-woven fabric. If chitosan particles enter the blood vessel through the wound, vessel occlusion, even a stroke will occur. The fabricating method can make chitosan fibers directly into a non-woven fabric, but the mechanical strength of the chitosan fabric would be weakened after the chitosan fiber absorbs blood or body fluid to swell and even dissolve. Consequently, the conventional bandage sticks to wounds easily, such that replacement with new dressings is difficult and even results in secondary injury. Furthermore, as the mechanical strength of conventional chitosan fiber is weak, weaving chitosan fibers into a bandage is also difficult.

SUMMARY OF THE INVENTION

To overcome the shortcoming of chitosan fibers' lack of strength, the objective of the present invention is to provide a method for fabricating a bandage having chitosan yarn with sufficient strength.

To achieve the above objective, the method in accordance with the present invention comprises the following steps:

(a) preparing multiple complex yarns each including chitosan fibers and rayon fibers;

(b) weaving solely the multiple complex yarns to form a preformed bandage;

(c) immersing the preformed bandage in an acid alcohol, and then washing the preformed bandage by alcohol to obtain an alcohol-washed bandage; and, (d) heating the alcohol-washed bandage to obtain the bandage.

According to the present invention, the term "solely", as used herein, refers to that the preformed bandage is consisted of said multiple complex yarns and without any other yarns that include any fiber other than chitosan fiber and rayon fiber.

Preferably, the chitosan fibers and rayon fibers are prepared separately by cotton carding, doubling, and twisting in regular turn.

Preferably, a concentration of the chitosan fibers in the complex yarns is between 10 wt % and 50 wt % of a total weight of the complex yarns.

Preferably, a concentration of the chitosan fibers in the complex yarns is between 20 wt % and 45 wt % of a total weight of the complex yarns.

Preferably, the acid alcohol comprises a weak acid, wherein the weak acid includes, but is not limited to, acetic acid, lactic acid, citric acid, succinic acid and glycolic acid.

Preferably, a concentration of the weak acid is between 3 wt % and 5 wt % of a total weight of the acid alcohol.

In a second aspect, the present invention provides a bandage prepared from the above-mentioned method, wherein the bandage is comprised of the complex yarns, wherein the complex yarns are each consisted of the chitosan fibers and the rayon fibers.

The bandage in accordance with the present invention is comprised of the complex yarns, wherein the complex yarns are each composed of chitosan fibers and rayon fibers. The bandage not only has increased tensile strength and promotes coagulation, but also decreases dissolution rate for medical dressings. The advantage of the bandage with the chitosan fibers in accordance with the present invention is that such bandage could be removed easily from a wound without leaving residue in the wound.

BRIEF DESCRIPTION OF THE DRAWINGS

FIG. 1 is a flow chart of the method for producing a bandage in accordance with the present invention.

DETAILED DESCRIPTION OF THE PREFERRED EMBODIMENTS

Other objectives, advantages and novel features of the invention will become more apparent from the following detailed description when taken in conjunction with the accompanying drawings.

As shown in FIG. 1, the present invention provides a method for fabricating a bandage having multiple chitosan yarns. At first, complex yarns each including chitosan yarns and rayon yarns are prepared. Preferably, in one embodiment, the concentration of the chitosan yarns is between 10 wt % and 50 wt % of the total weight of the complex yarns. More preferably, the concentration of the chitosan yarns is between 20 wt % and 45 wt % of the total weight of the complex yarns. Most preferably, the concentration of the chitosan yarns is between 30 wt % and 40 wt % of the total weight of the complex yarns.

The complex yarns in accordance with the present invention could be prepared by the following method. For example, the complex yarns each include chitosan fibers and rayon fibers, wherein the chitosan fibers are prepared by wet spinning, and the rayon fibers are prepared by cotton carding. Then the complex yarns are formed by doubling and twisting the chitosan fibers and rayon fibers.

Second, the multiple complex yarns are woven excluding other yarns to form a preformed bandage.

Third, the preformed bandage is immersed in an acid alcohol, and then the amino group of the preformed bandage is changed to ammonium group, such that the ammonium group can coagulate red blood cell and blood platelets on a surface of the wound. Preferably, the acid alcohol comprises a weak acid, and a concentration of the weak acid is between 3 wt % and 5 wt % of the total weight of the complex yarns. Preferably, the weak acid is acetic acid, lactic acid, citric acid, succinic acid or glycolic acid. Preferably, the incubation time of the preformed bandage immersed into the acid alcohol is about 30 minutes. After immersing, the bandage is washed by alcohol to remove the weak acid and to obtain an alcohol-washed bandage.

Finally, the alcohol-washed bandage is heated to obtain the bandage.

The yarns of the bandage obtained from the above method comprise complex yarns, wherein the complex yarns are each composed of chitosan fibers and rayon fibers. Moreover, after the preformed bandage is immersed in the acid alcohol, the chitosan fiber of the bandage can promote coagulation.

There are some tests as described below utilizing various chitosan contents of the complex yarns to prepare bandages by the above-mentioned method.

Example 1. The Coagulation Test

100 µl blood was separately dropped on bandage samples of the present invention having various chitosan contents, samples of commercially available products having functions of promoting coagulation, control sample of non-woven fabrics having chitosan fibers or rayon fibers. Waiting for about 30 seconds to 240 seconds, the above-mentioned samples were each put into 10 ml physiologic saline to stir for 120 seconds to lyse the blood from the samples, and the absorbance of the samples were measured at 540 nm. 100 µl blood and 10 ml physiologic saline was defined as a standard sample and the absorbance at 540 nm was defined as 1. Then, the absorbances of the samples were compared to obtain a relative absorbance to quantify the hemolytic dose of each sample. A higher relative absorbance means a higher hemolytic dose and thus decreased activity of coagulation.

TABLE 1

The hemolytic doses of the bandages samples woven of complex yarns, commercially available products, and control sample

| sample | | amount of chitosan (wt %) | incubation time (seconds) | | | |
|---|---|---|---|---|---|---|
| | | | 30 | 60 | 120 | 240 |
| the bandage comprised of complex yarns | 1 | 10 | 0.17 | 0.12 | 0.01 | 0.08 |
| | 2 | 20 | 0.14 | 0.11 | 0.08 | 0.05 |
| | 3 | 30 | 0.11 | 0.07 | 0.06 | 0.03 |
| | 4 | 40 | 0.09 | 0.06 | 0.06 | 0.03 |
| | 5 | 45 | 0.13 | 0.09 | 0.09 | 0.07 |
| | 6 | 50 | 0.17 | 0.11 | 0.13 | 0.09 |
| | 7[1] | 100 | 0.65 | 0.45 | 0.21 | 0.27 |
| HemCon ® bandage[2] | | 14 | 0.24 | 0.22 | 0.17 | 0.16 |
| Celox ® bandage[3] | | 22 | 0.31 | 0.21 | 0.15 | 0.17 |
| Celox ® styptic powder[4] | | >95 | 0.44 | 0.34 | 0.17 | 0.17 |
| Conventional non-woven fabric having chitosan fibers | | 100 | 0.16 | 0.10 | 0.08 | 0.08 |
| rayon fiber only[5] | | 0 | 0.69 | 0.70 | 0.64 | 0.70 |

[1] the bandage was comprised of 100 wt % chitosan long fibers
[2] the bandage was prepared by blending PET fibers and rayon fibers, coating the chitosan solution, and heating in regular turn.
[3] the bandage was prepared by coating chitosan powder onto non-woven cotton fabrics.
[4] the styptic powder was composed of chitosan powder.
[5] the bandage was consisted of rayon fibers.

The results of the hemolytic dose test were presented in Table 1. The results of the samples 1 to 7 demonstrated that while the contents of chitosan were between 10 wt % and 100 wt %, the hemolytic dose reached the minimum when the chitosan amount ranged from about 30 wt % to 40 wt %, and the variation tendency of the hemolytic dose was decreasing first and then increasing. Further, the blood coagulation by the complex yarns having the chitosan content ranging from 30 wt % to 40 wt % was the best of all. Besides, comparing the hemolytic doses of the bandages having chitosan fiber and of the commercially available products, the coagulation by sample 1 having 10 wt % chitosan fiber was better than the commercially available HemCon® bandage having 14 wt % chitosan; the coagulation by sample 2 having 20 wt % chitosan fiber was twice the commercially available Celox® bandage having 22 wt % chitosan and close to the conventional non-woven fabric having chitosan fibers, not to mention the commercially available Celox® styptic powder that has more than 95 wt % chitosan. Particularly, due to lower efficiency of solution absorbance, the sample 7 comprised of all chitosan long fibers had decreasing coagulation. Thus, the coagulation efficiency of the bandage composed of complex yarns having chitosan fibers and rayon fibers was superior beyond expectation.

Example 2. The Lytic Test 0.5 g of the bandage samples, of the samples of commercially available products, and of the control sample each containing a different amount of chitosan were separately placed into sample bottles. 20 ml physiologic saline was added into each sample bottle. Each sample bottle was stirred for 10 minutes to 60 minutes. Then, the solutions from each sample bottle were filtered, heated, and weighed to calculate the dissolution rates of the above-mentioned samples.

TABLE 2

The dissolution rate of the bandage woven of complex yarns, the commercially available products and control sample

| sample | | amount of chitosan (wt %) | stirring time (minutes) | | | |
|---|---|---|---|---|---|---|
| | | | 10 | 20 | 30 | 60 |
| the bandage comprised of complex yarns | 1 | 10 | 2 | 4 | 4 | 4 |
| | 2 | 20 | 2 | 5 | 5 | 6 |
| | 3 | 30 | 4 | 6 | 6 | 7 |
| | 4 | 40 | 6 | 7 | 9 | 10 |
| | 5 | 45 | 6 | 9 | 9 | 11 |
| | 6 | 50 | 8 | 10 | 12 | 14 |
| | 7[1] | 100 | 10 | 15 | 21 | 29 |
| commercially available HemCon ® bandage[2] | | 14 | 9 | 10 | 10 | 10 |
| commercially available Celox ® bandage[3] | | 22 | 9 | 10 | 10 | 12 |
| commercially available Celox ® styptic powder[4] | | >95 | 100 | 100 | 100 | 100 |
| conventional non-woven fabrics having chitosan fibers | | 100 | 46 | 58 | 66 | 78 |

[1] the bandage was comprised of 100 wt % chitosan long fibers
[2] the bandage was prepared by blending PET fibers and rayon fibers, coating the chitosan solution, and heating in regular turn.
[3] the bandage was prepared by coating chitosan powder onto cotton non-woven fabrics.
[4] the styptic powder was composed of chitosan powder.

The results of dissolution rate were presented in Table 2. The results of the samples 1 to 7 demonstrated that while the contents of chitosan were between 10 wt % and 100 wt %, the dissolution rates were increasing in compliance with the increasing chitosan. While the contents of chitosan in the bandage and in the commercially available products were equal, dissolution rates were increasing in accordance with the stirring time. When the contents of chitosan ranged from 10 wt % to 40 wt %, the dissolution rate was within 10 wt %. Comparing the sample 7, commercially available Celox® styptic powder, and the conventional non-woven fabric having chitosan fibers, though the contents of chitosan were more than 95 wt % or 100 wt %, the dissolution rates of each of them were different. Wherein the commercially available Celox® styptic powder had the highest dissolution rate, followed by the conventional non-woven fabric having chitosan fibers, and the sample 7 had the lowest dissolution rate. Thus, dissolution rate would be affected by the shape of chitosan, and dissolution rate was decreasing in coordination with increasing length of chitosan.

Example 3. The Tensile Strength Test

Bandages made of complex yarns having various chitosan contents, samples of commercially available products, and control sample of non-woven fabrics having chitosan fibers or only rayon fibers were separately cut into 7 cm×2 cm. Each sample was clamped by 2 cm at both ends with 3 cm unclamped between the clamped ends, stretched by 60 mm/min constant speed until breaking to measure tensile strength of the above-mentioned samples.

TABLE 3

The tensile strength of the bandage woven of complex yarns, the commercially available products and the control sample

| Sample | | amount of chitosan (wt %) | Tensile strength (kgf/cm$^2$) |
| --- | --- | --- | --- |
| the bandage comprised of complex yarns | 1 | 10 | 30.6 |
| | 2 | 20 | 28.2 |
| | 3 | 30 | 26.8 |
| | 6 | 50 | 18.4 |
| Celox ® bandage* | | 22 | 18.1 |
| non-woven fabric having chitosan fibers | | 100 | 14.6 |
| rayon fiber only | | 0 | 31.3 |

*prepared by coating chitosan powder onto cotton non-woven fabrics.

The results of the samples 1 to 3 and 6 were demonstrated in Table 3. The tensile strength was decreasing in accordance with the increasing chitosan. The tendency also could be demonstrated by that the non-woven fabric having chitosan fibers had the minimum tensile strength and the rayon fibers had the maximum tensile strength. Particularly, the tensile strength of sample 6 having 50 wt % chitosan is superior to the tensile strength of the commercially available Celox® bandage. Thus, the tensile strength of the bandage prepared by the above-mentioned method is fairly good.

Example 4. The Cytotoxic Test

ISO 10993-5 test for in vitro cytotoxicity was used to test biocompability of the medical material by cell culture. The ISO 10993-5 test comprised direct contact method, agar diffusion method, and MEM elution, and herein the method adopted was the direct contact method. Only the cells located under the above-mentioned samples were injured. Thus, the above-mentioned samples were slightly cytotoxic within a bearable range for adoption on humans.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A method for fabricating a bandage, consisting steps of:
   (a) preparing multiple complex yarns each including chitosan fibers and rayon fibers;
   (b) weaving solely the multiple complex yarns to form a preformed bandage;
   (c) immersing the preformed bandage in an acid alcohol, and then washing the preformed bandage by alcohol to obtain an alcohol-washed bandage; and
   (d) heating the alcohol-washed bandage to obtain the bandage;
   wherein a concentration of the chitosan fibers is between 10 wt % and 50 wt % of a total weight of the complex yarns;
   wherein the bandage has a hemolytic dose that decreases from 0.09~0.17 to 0.03~0.09 after interacting with blood for a time period of 30 seconds to 240 seconds, and a dissolution rate that increases from 2 wt %~6 wt % to 4 wt %~11 wt % after soaking in phyiological fluid for a time period of 10 minutes to 60 minutes, having coagulation function.

2. The method according to claim 1, wherein the concentration of the chitosan fibers is between 20 wt % and 45 wt % of the total weight of the complex yarns.

3. The method according to claim 1, wherein the acid alcohol comprises a weak acid, wherein the weak acid is acetic acid, lactic acid, citric acid, succinic acid or glycolic acid.

4. The method according to claim 3, wherein a concentration of the weak acid is between 3 wt % and 5 wt % of a total weight of the acid alcohol.

5. A bandage prepared by a method consisting steps of:
   (a) preparing multiple complex yarns each including chitosan fibers and rayon fibers;
   (b) weaving solely the multiple complex yarns to form a preformed bandage;
   (c) immersing the preformed bandage in an acid alcohol, and then washing the preformed bandage by alcohol to obtain an alcohol-washed bandage; and
   (d) heating the alcohol-washed bandage to obtain the bandage;
   wherein the concentration of the chitosan fibers is between 10 wt % and 50 wt % of a total weight of the complex yarns;
   wherein the bandage has a hemolytic dose that decreases from 0.09~0.17 to 0.03~0.09 after interacting with blood for a time period of 30 seconds to 240 seconds, and a dissolution rate that increases from 2 wt %~6 wt % to 4 wt %~11 wt % after soaking in phyiological fluid for a time period of 10 minutes to 60 minutes, having coagulation function.

6. The bandage as claimed in claim 5, wherein the concentration of the chitosan fibers is between 20 wt % and 45 wt % of the total weight of the complex yarns.

7. The bandage as claimed in claim 5, wherein the acid alcohol comprises a weak acid, wherein the weak acid is acetic acid, lactic acid, citric acid, succinic acid or glycolic acid.

8. The bandage as claimed in claim 7, wherein a concentration of the weak acid is between 3 wt % and 5 wt % of a total weight of the acid alcohol.

9. The bandage as claimed in claim 5, wherein the bandage has a tensile strength from 18.4 kgf/cm$^2$ to 30.6 kgf/cm$^2$.

* * * * *